(12) United States Patent
Yoshimi et al.

(10) Patent No.: US 6,280,392 B1
(45) Date of Patent: Aug. 28, 2001

(54) INFANT CONDITION MONITORING SYSTEM AND METHOD USING LOAD CELL SENSOR SHEET

(75) Inventors: Tomohisa Yoshimi, Gamagori; Masahiko Ito, Nagoya; Kenichi Yanai, Nisshin; Tomomasa Sato, Abiko; Tatuya Harada, Tachikawa; Taketoshi Mori, Kawasaki, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/361,237

(22) Filed: Jul. 27, 1999

(30) Foreign Application Priority Data

| Jul. 29, 1998 | (JP) | ................................................ | 10-214571 |
| Jun. 1, 1999 | (JP) | ................................................ | 11-153527 |

(51) Int. Cl.$^7$ ...................................................... A61B 5/08
(52) U.S. Cl. ........................................... 600/534; 600/529
(58) Field of Search .................................... 600/529, 534, 600/535, 536, 531, 532, 533, 538, 537; 73/23.3

(56) References Cited

U.S. PATENT DOCUMENTS

| 3,760,794 | * | 9/1973 | Basham | ................................. | 600/535 |
| 3,898,981 | * | 8/1975 | Basham | ................................. | 600/535 |
| 3,996,922 | * | 12/1976 | Basham | ................................. | 600/535 |
| 4,245,651 | * | 1/1981 | Frost | ..................................... | 600/300 |
| 4,471,354 | * | 9/1984 | Smith | ..................................... | 600/534 |
| 4,509,527 | * | 4/1985 | Fraden | .................................. | 600/534 |
| 4,862,144 | * | 8/1989 | Tao | ......................................... | 600/534 |
| 4,884,578 | * | 12/1989 | Morgenstern | ......................... | 600/534 |
| 4,926,866 | * | 5/1990 | Lee | ........................................ | 600/301 |
| 5,423,328 | * | 6/1995 | Gavish | .................................. | 600/534 |
| 5,448,996 | * | 9/1995 | Bellin et al. | ........................... | 600/529 |
| 5,479,939 |   | 1/1996 | Ogino . |
| 5,825,293 | * | 10/1998 | Ahmed et al. | ......................... | 600/529 |

FOREIGN PATENT DOCUMENTS

| 1908652 | * | 9/1970 | (DE) . |
| 3444635 | * | 6/1986 | (DE) . |
| 2116725 | * | 9/1983 | (GB) . |
| 49-107197 |   | 10/1974 | (JP) . |
| 8-215175 |   | 8/1996 | (JP) . |
| 11-28195 |   | 2/1999 | (JP) . |
| 88/02237 | * | 4/1988 | (WO) . |
| 93/08734 |   | 5/1993 | (WO) . |

\* cited by examiner

*Primary Examiner*—John P. Lacyk
*Assistant Examiner*—Navin Natnithithadha
(74) *Attorney, Agent, or Firm*—Pillsbury Winthrop LLP

(57) ABSTRACT

An infant condition monitoring system has a sensor sheet including uniformly arranged plural pressure sensitive load cells. An ECU in an electronic unit connected to the sensor sheet calculates an infant's breathing signal, sleeping posture and weight data. Those signal and data are converted into data signals to modulate a carrier signal thereby. A transmitter in the electronic unit transmits a radio signal resulting from the modulation. A monitoring unit is constructed to be carried by a care provider. A receiver in the monitoring unit demodulates the received radio signal. An ECU reproduces the data signals including the breathing signal, sleeping posture and weight data, and determines a respiration rate, sleeping posture and weight. A display displays the respiration rate, sleeping posture and weight, and a speaker produces an output sound in correspondence with the breathing signal.

22 Claims, 8 Drawing Sheets

INFANT CONDITION MONITORING SYSTEM AND METHOD USING LOAD CELL SENSOR SHEET

CROSS REFERENCE TO RELATED APPLICATION

This application relates to and incorporates herein by reference Japanese Patent Applications No. 10-214571 filed on Jul. 29, 1998, and No. 11-153527 filed on Jun. 1, 1999.

BACKGROUND OF THE INVENTION

1. Field of the Invention

The present invention relates to an infant condition monitoring system for monitoring the health condition of an infant sleeping on a bed.

2. Related Art

It is a recent social problem that infants die suddenly while sleeping. This is known as sudden infant death syndrome (SIDS) or infant apnea syndrome.

It is proposed to monitor breathing of an infant by monitoring breathing from difference in temperatures of inhaled air and exhaled air detected by a temperature sensor attached to the infant's nasal cavity. It is also proposed to monitor breathing, using a strain gage or the like, by expansion and contraction of a belt attached around the infant's chest.

Those proposed cells require electrical signal wires which connect the sensing cell and a monitoring cell. The signal wires are likely to be wrapped around the infant's neck and to choke the infant's neck when the infant rolls. Further, it is very likely that the infant feels uncomfortable with the sensing cell and takes it away.

SUMMARY OF THE INVENTION

It is therefore an object of the present invention to provide an infant condition monitoring system for monitoring the health condition of a sleeping infant without disturbing.

According to the present invention, a sensor sheet having uniformly arranged plural load cells is placed under an infant to be monitored. An infant's breathing signal is formed from load signals of the load cells, and an infant's breathing condition such as a respiration rate is determined from the breathing signal. An infant's weight and sleeping posture are also determined from the load signals of the load cells. Those determined items are reported on a display and a breathing sound is produced by a speaker from the breathing signal.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

The present invention will be described in further detail with reference to its preferred embodiments.

(First Embodiment)

Figure 1:
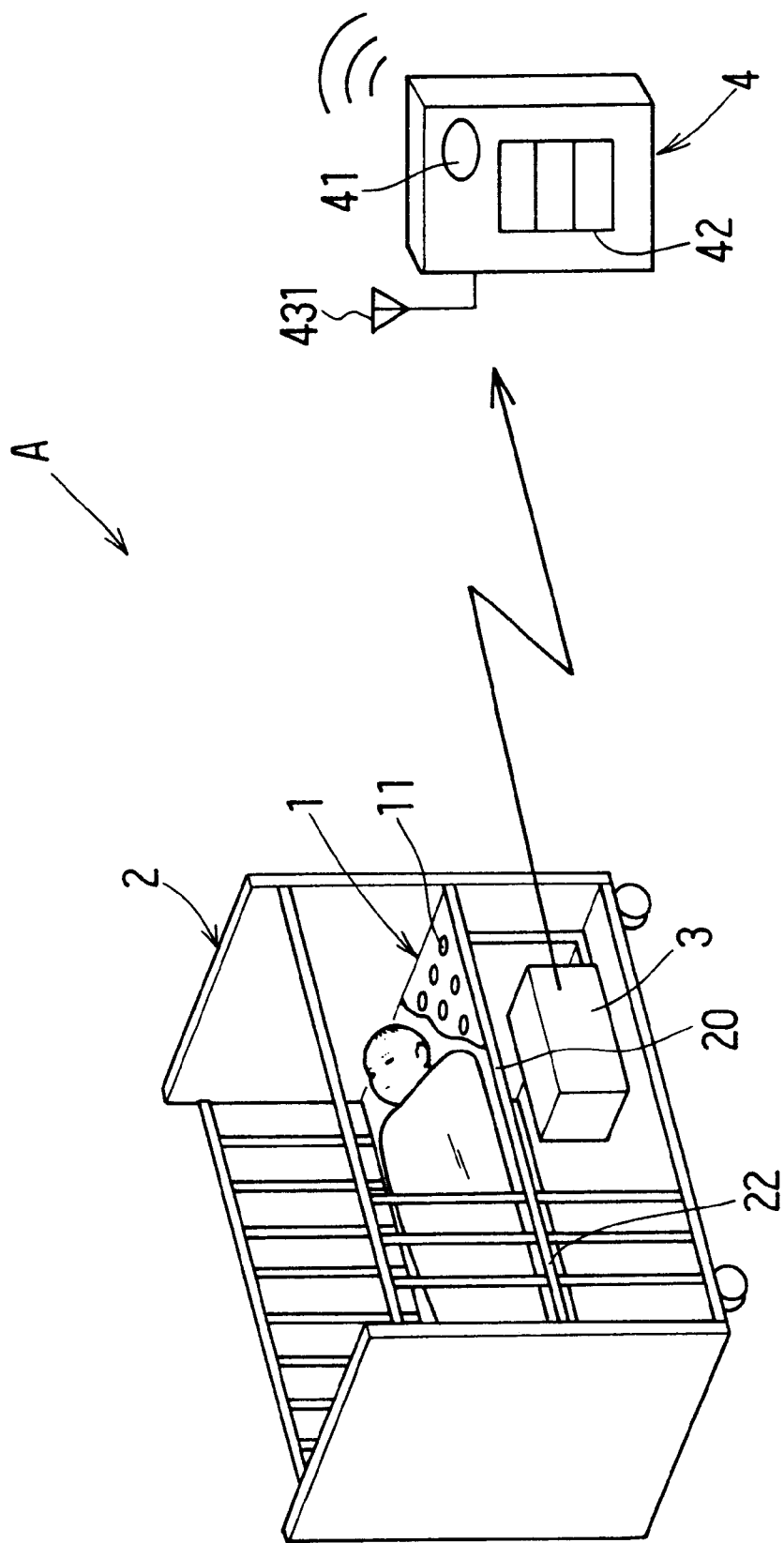
FIG. 1 is a schematic view showing an infant condition monitoring system according to a first embodiment of the present invention.

In FIG. 1, an infant condition monitoring system A includes a sensor sheet 1 placed on a baby bed 2, an electronic unit 3, and a portable monitoring unit 4 with a speaker 41 and a display 42. The electronic unit 3 is positioned in a lower space under a bed floor 22 to communicate with the monitoring unit 4 through a radio signal.

The sensor sheet 1 has plural (210) pressure sensitive cells 11 disposed at equal intervals therein, and is placed underneath a mattress 20 on the bed floor 22. Each pressure sensitive cell 11 has a characteristics in which the electric resistance decreases as the applied load weight increases. The sensor sheet 1 is electrically connected to the electronic unit 3.

Figure 2:
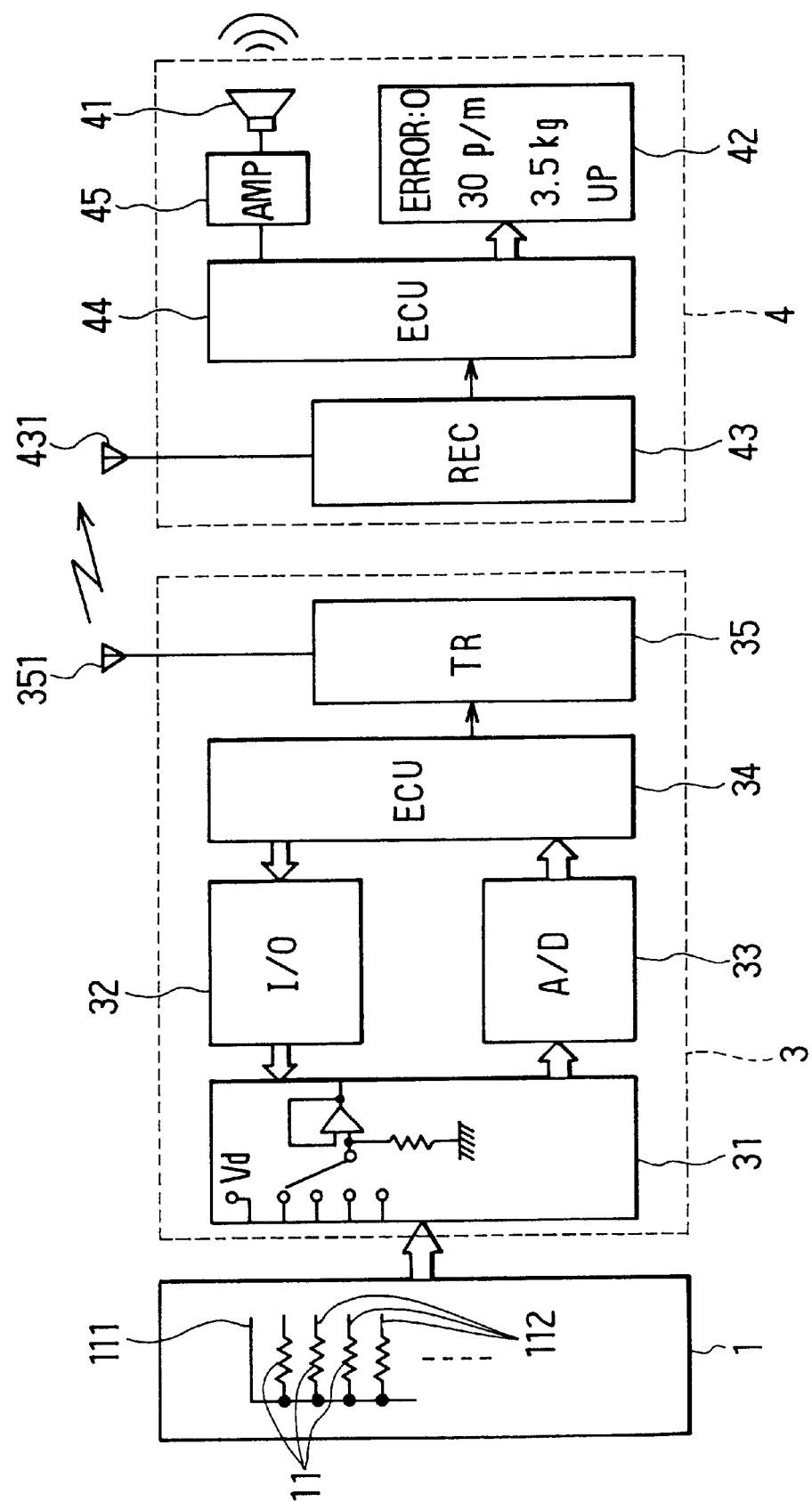
FIG. 2 is a block diagram showing the infant condition monitoring system according to the first embodiment.

As shown in FIG. 2, the electronic unit 3 has an analog multiplexer 31, a parallel I/O (input/output)32, an A/D (analog/digital) converter 33, an ECU (electronic control unit) 34 including a microcomputer, and a radio transmitter 35 connected to an antenna 351.

Each pressure sensitive cell 11 has one end 111 connected to a power supply terminal Vd of the analog multiplexer 31 and the other end 112 connected to electronic contact of the multiplexer 31. The multiplexer 31 is controlled by switching signals of the parallel I/O 32 to receive sequentially analog load signals of the pressure sensitive cells 11. The multiplexer 31 may be operated at 70 Hz, for instance. The multiplexer 31 thus converts the analog load signals received in parallel from the sensor sheet 1 into serial analog load signals, and applies the serial signals to the A/D (analog/digital) converter 33. The A/D converter 33 converts the serial analog signals to corresponding digital signals.

The ECU 34 determines an infant's breathing, sleeping posture and weight from the digital signals. The radio transmitter 35 converts the determined breathing, sleeping and weight into corresponding data signals, modulates carrier wave by the data signals, and transmits modulated radio signals (400 MHz, 10 mW) from the antenna 351.

The monitoring unit 4 has, in addition to the speaker 41 and the display 42, a radio receiver 43 connected to an antenna 431, an ECU 44 including a microcomputer, and an amplifier 45. The monitoring unit 4 has a built-in battery, and is sized and weighted to be carried by an infant care provider such as his/her mother, nurse or the like.

The receiver 43 subjects the modulated radio signals received at the antenna 431 to the wave-detection and demodulates the data signals. The ECU 44 determines the infant's breathing, sleeping posture, weight, and respiration rate from the data signals. The display 42 displays the respiration rate, sleeping posture and weight. The amplifier 45 has a VCO (voltage-controlled oscillator), which oscillates at higher frequencies as the magnitude of the infant's breathing or respiration increases, and drives the speaker in response to the VCO output signal.

The electronic unit 3, particularly the microcomputer of the ECU 34, is programmed to execute the following processing.

Figure 3:
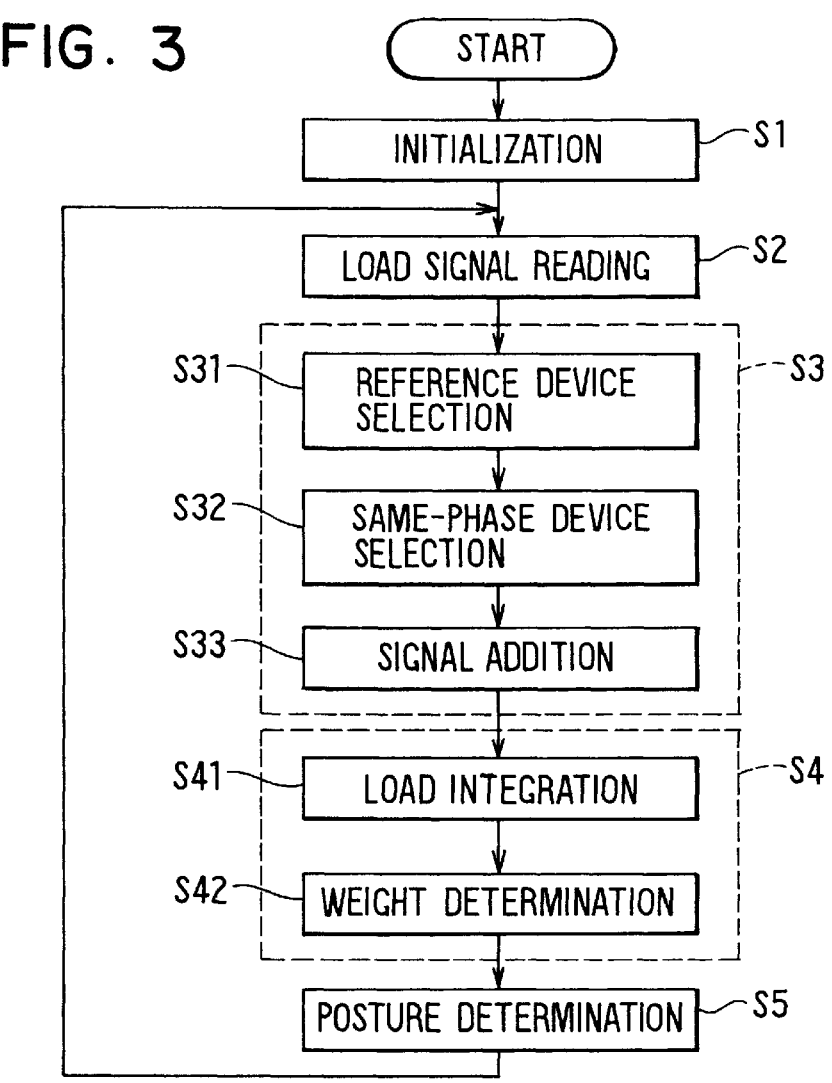
FIG. 3 is a flow diagram showing the operation processing of a control unit used in the infant condition monitoring system according to the first embodiment.

First, as shown in FIG. 3, the ECU 34 initializes at step S1 its RAM and associated circuits such as the parallel I/O 32, A/D converter 33 and the like to respective initial setting. The ECU 32 then reads in at step S2 the digital signals each indicating the load applied to the corresponding pressure sensitive cell 111 of the sensor sheet 1.

At step S3 (steps S31–S33), the ECU 34 forms an infant's breathing signal based on changes in distribution of loads which is caused by up-down movements of a diaphragm responsive to the infant's breathing.

Specifically, at step S31, the load signal from each pressure sensitive cell 11 is subjected to filtering through a band pass filter having a pass band at around a specified frequency corresponding to breathing. Then, at step S32, one of the pressure sensitive cells 11 which produces the load signal with the largest magnitude (largest load change) is selected as a reference cell. For instance, the reference cell may be determined by subjecting the filtered load signals to frequency analysis (FFT: Fourier frequency transform) and selecting the one which has the largest power spectrum in the specified frequency range.

Here, the specified frequency range is set widely to cover both the infant's normal breathing condition (15–25 times per minute) but also surrounding breathing condition outside of the normal breathing condition. For instance, the specified frequency range is set to 0.15 Hz–0.55 Hz which corresponds to 9–33 times per minute, although the frequency range corresponding to the normal breathing condition is 0.25 Hz–0.42 Hz.

Next, at step S32, a correlation function among the load signals of the reference cell and other cells 11 is determined to select the pressure sensitive cells which produce the load signals in substantially the same phase relation with that of the reference cell. Here, the same phase signals are defined as the signals which have the phase difference of less than ±45°. The same phase signals may be defined as the signals which have the phase difference of less than ±90°.

Figure 4A:
FIGS. 4A and 4B are timing diagrams showing infant's breathing signals produced in the infant condition monitoring system according to the first embodiment.
Figure 4B:
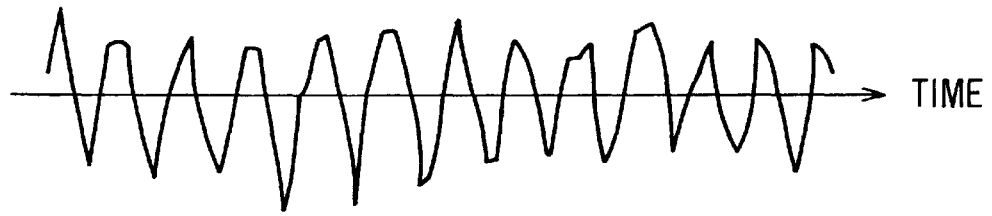

Then, at step S33, the load signal of the reference cell and the load signals of the selected pressure sensitive cells 11 which are in the same phase relation with that of the reference cell are added to form the breathing signal as shown in FIGS. 4A and 4B. FIG. 4A shows the breathing signal when the load signals of all the pressure sensitive cells 11 are added, while FIG. 4B shows the breathing signal when only the load signals in the same phase relation are added. Thus, the breathing signal is free of signal noises which are likely to be included due to infant's body movements other than his/her breathing, and represents the infant's breathing accurately.

According to the above processing, the breathing signal having a frequency corresponding to 9–33 times of breathing per minute is formed. However, such a breathing signal which corresponds to the number of respiration will not be formed when the infant is in the apnea or breathless condition or in the abnormal breathing condition. In this instance, the reference cell cannot be selected, or the magnitude of the breathing signal resulting from the addition of the same phase signals remains lower than a threshold level. Thus, the infant's breathing condition can be determined to be abnormal.

Figure 5:
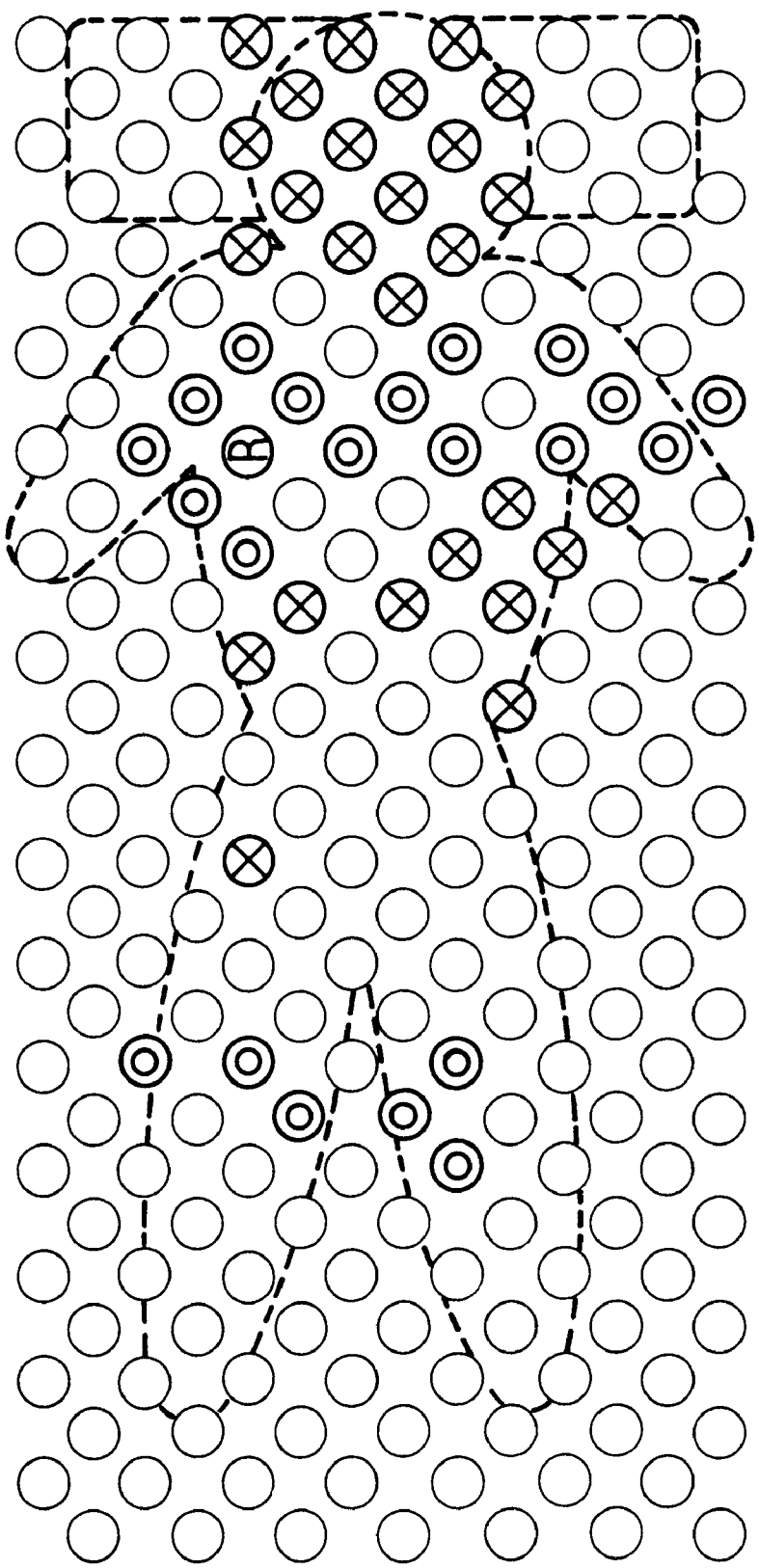
FIG. 5 is a schematic view showing output signal conditions of pressure sensitive cells used in the infant condition monitoring system according to the first embodiment.

FIG. 5 shows an exemplary distribution of the load signals of the pressure sensitive cells under the condition that the infant is inhaling. In this figure, the reference cell is denoted by a circled R. The cells which are in the same phase relation with the reference cell are denoted by double circles, while the cells which are in the opposite phase relation with the reference cell are denoted by circled Xs. The opposite phase signal is defined as the signal having a phase difference in the range of 180±45° from the signal of the reference cell. This phase difference range may be set to 180±45°. The remaining cells which do not produce load signals are denoted by single circles. In this instance, the reference cell is located just above the infant's chest.

As evident from FIG. 5, the pressure sensitive cells around the reference cell produce the same phase signals, while the pressure sensitive cells around the head and stomach produce the opposite phase signals. Therefore, the same phase signals and the opposite phase signals are only mixed when the load signals of all the pressure sensitive cells 11 are added, thus resulting in the signal waveform of the breathing signal shown in FIG. 4A. On the contrary, the signal waveform of the breathing signal accurately corresponds to the breathing condition as shown in FIG. 4B, when the pressure sensitive cells which produce the load signals in the same phase relation with that of the reference cell are selected and only the same phase signals of those selected cells are added.

It is also possible at steps S32 and S33 to select the load signals in the opposite phase in place of the load signals in the same phase, invert those selected signals by shifting the opposite phase signals by 180° and add those inverted signals to the load signal of the reference cell. It is further possible to add both the same phase signals and the inverted opposite phase signals to the load signal of the reference cell.

The ECU 34 then determines at step S4 (steps S41 and S42) the weight of the infant. Specifically, all the load signals of the pressure sensitive cells 11 are added or integrated at step S41, and the weight is determined by multiplying a specified coefficient k1 to the integrated load. It is preferred to subtract the weight of a blanket and closings over the infant from the above-calculated total weight.

Figure 6:
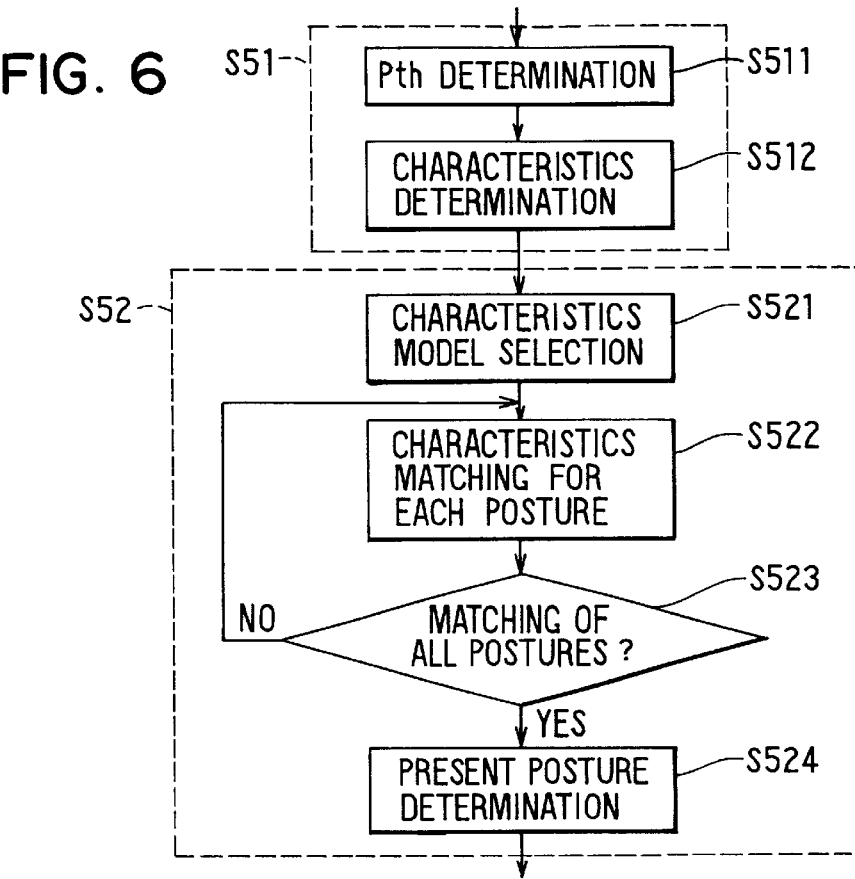
FIG. 6 is a flow diagram showing the determination processing of infant's sleeping posture in the infant condition monitoring system according to the first embodiment.

The ECU 34 further determines at step S5 (steps S51 and S52) the sleeping posture of the infant. That is, as shown in FIG. 6, a sleeping posture characteristics of the infant is determined at step S51, and a sleeping posture is determined at step S52 from the determined characteristics.

Specifically, first at step S511, a threshold Pth is calculated from the following equation (1), in which Pi denotes each load signal with i being from 1 to 210.

$$Pth = \frac{\sum_{i=1}^{210} P_i}{210} \times k \qquad \text{Equation (1)}$$

This threshold Pth is proportional to the average of the applied loads and is necessary for calculating the sleeping posture characteristics. The coefficient k may be 0.5 although not limitative.

At step S512, the sleeping posture characteristics is calculated by comparing each load signal Pi with the threshold Pth.

At step S522, a characteristics model is determined by selecting it at random from a variety of models prestored for each of several sleeping postures. At the following step S523, it is checked whether the sleeping posture characteristics determined at step S512 matches with the selected characteristics model, thereby determining correlation for each sleeping posture.

Here, the correlation may be determined by the following equation (2) with f, g and D being defined as the present posture characteristics data, each selected posture characteristics model data, and the exclusive range of coverage of g, respectively. The equation (2) thus represents the degree of disagreement between the posture characteristics data and each selected characteristics model data, because $\iint_d g^2$ is known and $\iint_d f^2$ is constant.

$$\iint_D (g-f)^2 = \iint_D g^2 + \iint_D f^2 - 2\iint gf \qquad \text{Equation (2)}$$

The following equation (3) will result when the above integration value is calculated for each movement (m, n) while moving g to possible locations in f.

$$\iint_D g(x,y)f(x+m,y+n)dxdy \qquad \text{Equation (3)}$$

Further, the following inequality relation (4) is derived by the use of Cauchy's inequality.

$$\iint_D g(x,y)f(x+m,y+n)dxdy \leq \sqrt{\iint_D g^2(x,y)dxdy \iint_D f^2(x+m,y+n)dxdy} \qquad \text{Equation (4)}$$

The integration value may be replaced with a sum value in the case of a digital image. Therefore, the equation (4) can be replaced with the following equation (5).

$$\sum\sum_{(I,j)\in D} g(I,j)f(I+m,j+n) \leq \sqrt{\left\{\sum\sum_{(I,j)\in D} g^2(I,j)\right\}\left\{\sum\sum f^2(I+m,j+n)\right\}} \qquad \text{Equation (5)}$$

Finally, the following equation (6) is derived by dividing the left term of the equation (5) by the right term of the same. This equation (6) represents a normalized correlation function.

$$R_{fg}(m,n) = \frac{\sum\sum_{(I,j)\in D} g(I,j)f(I+m,j+n)}{\sqrt{\left\{\sum\sum_{(I,j)\in D} g^2(I,j)\right\}\left\{\sum\sum_{(I,j)\in D} f^2(I+m,j+n)\right\}}} \qquad \text{Equation (6)}$$

Thus, all the possible sleeping postures (including joint angles) which the infant will take can be determined by the above correlation function (6).

Then at step S523, it is checked whether all the correlation functions have been calculated. If YES, the present sleeping posture is determined at step S524 from one correlation function which matches most with the selected posture model.

The ECU 34 then applies the data signal, which includes the breathing signal data, weight data and sleeping posture data as well as communication error data, to the radio transmitter 35 to be transmitted to the monitoring unit 4 through a corresponding modulated radio signal.

Figure 7:
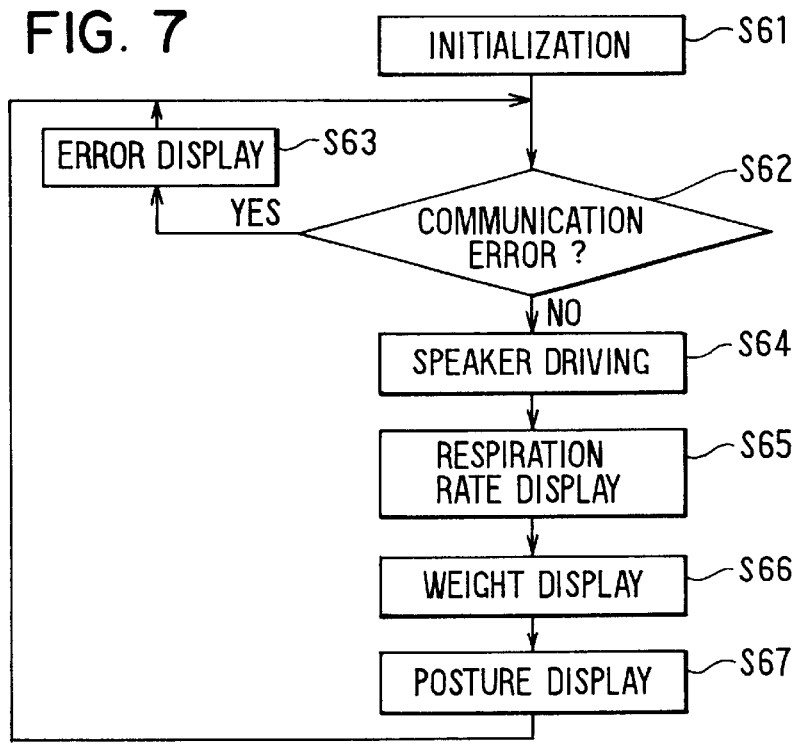
FIG. 7 is a flow diagram showing the operation processing of an alarm cell used in the infant condition monitoring system according to the first embodiment.

The monitoring unit 4, particularly the microcomputer of the ECU 44, is programmed to execute the following processing as shown in FIG. 7.

The ECU 44 first initializes its internal circuits at step S61 when a power switch of the monitoring unit 4 is turned on. The ECU 44 then checks at step S62 whether the data signal included in the radio signal, which is received at the antenna 431 and wave-detected and demodulated by the radio receiver 43, is normal. This checking may be accomplished by a parity check.

If NO, that is, when no communication error exists, the ECU 44 extracts the breathing data, sleeping posture data and weight data from the data signal, and proceeds to step S64. If YES, that is, when communication error exists, the ECU 44 drives the display 42 to display the communication error.

The ECU 44 drives at step S65 the speaker 41 through the amplifier 44 at the frequency of its VCO circuit which is varied in response to the extracted breathing data. The speaker 41 thus varies its output sound tone to inform the breathing condition of the infant.

The ECU 44 also drives the display 42 at steps S65, S66 and S67. Specifically, the respiration rate, which indicates the number of breathing per minute, is displayed at step S65. The respiration rate may be calculated by subtraction processing of the breathing data and counting the number of inflection points. The weight is displayed at step S66 in response to the received weight data, and the sleeping posture is displayed at step S67 in response to the received posture data.

The above first embodiment provides the following advantages.

(a) The care provider is enabled to monitor the infant's condition through the displayed contents (respiration rate, weight, sleeping posture, etc.) on the display 42 at a place away from the infant, while paying attention to changes in the tone of output sound provided from the speaker 41. That is, any abnormal condition of the infant, which includes abnormal breathing, unnatural sleeping posture, falling down from the bed or the like, can be detected at the earliest time by the care provider. Thus, if necessary, the care provider can responsively take preventive measures or emergency or first-aid actions. Further, the work load of the care provider can be reduced.

(b) The sensor sheet 1 can be disposed underneath the mattress 20 with ease, and does not disturb nor hurt the infant at all.

(c) The breathing signal is formed from the load signal of the reference cell and the load signals in the same phase relation therewith. Thus, the breathing signal can be formed to closely match the infant's breathing pattern and be less influenced by noise. As a result, the respiration rate can be calculated and displayed accurately, and the breathing condition can be reproduced from the speaker 41 closely to the actual breathing of the infant.

(d) It is possible to record the infant's condition such as weight automatically at regular time intervals by the use of electronic data. This is particularly of advantage for new born babies, because it is not necessary to move them from a bed to a weight scale. Further, this will not cause insufficient sleep nor stresses.

(Second Embodiment)

Figure 8:
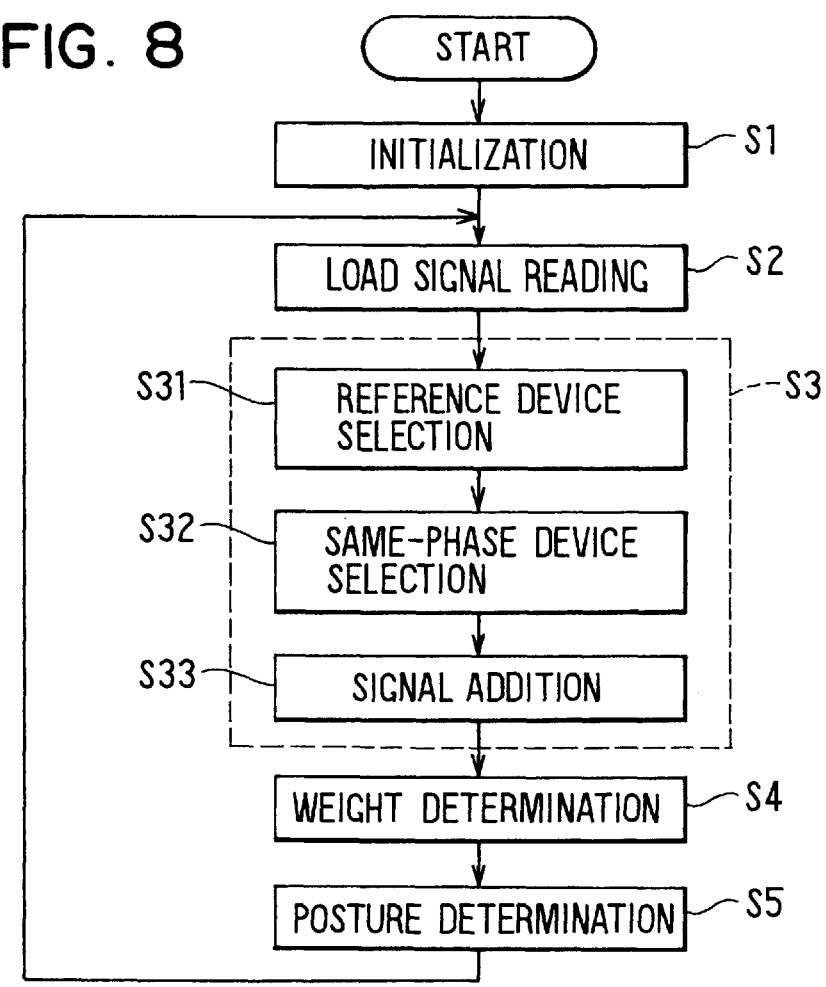
FIG. 8 is a flow diagram showing the operation processing of a control unit used in an infant condition monitoring system according to a second embodiment of the present invention.
Figure 9:
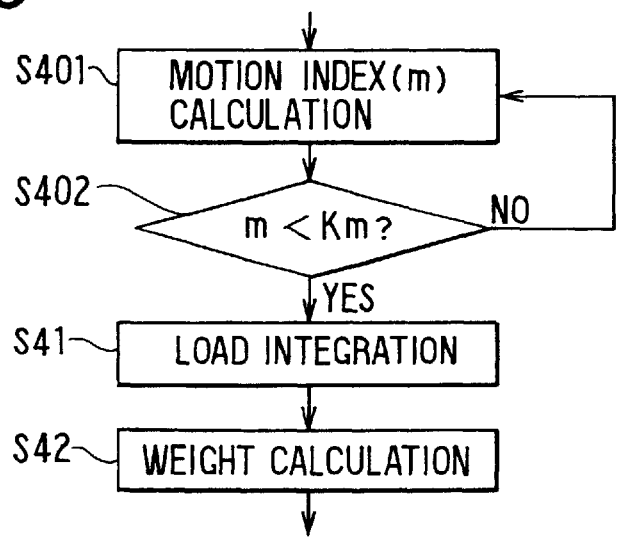
FIG. 9 is a flow diagram showing the determination processing of infant's weight in the infant condition monitoring system according to the second embodiment.
Figure 10:
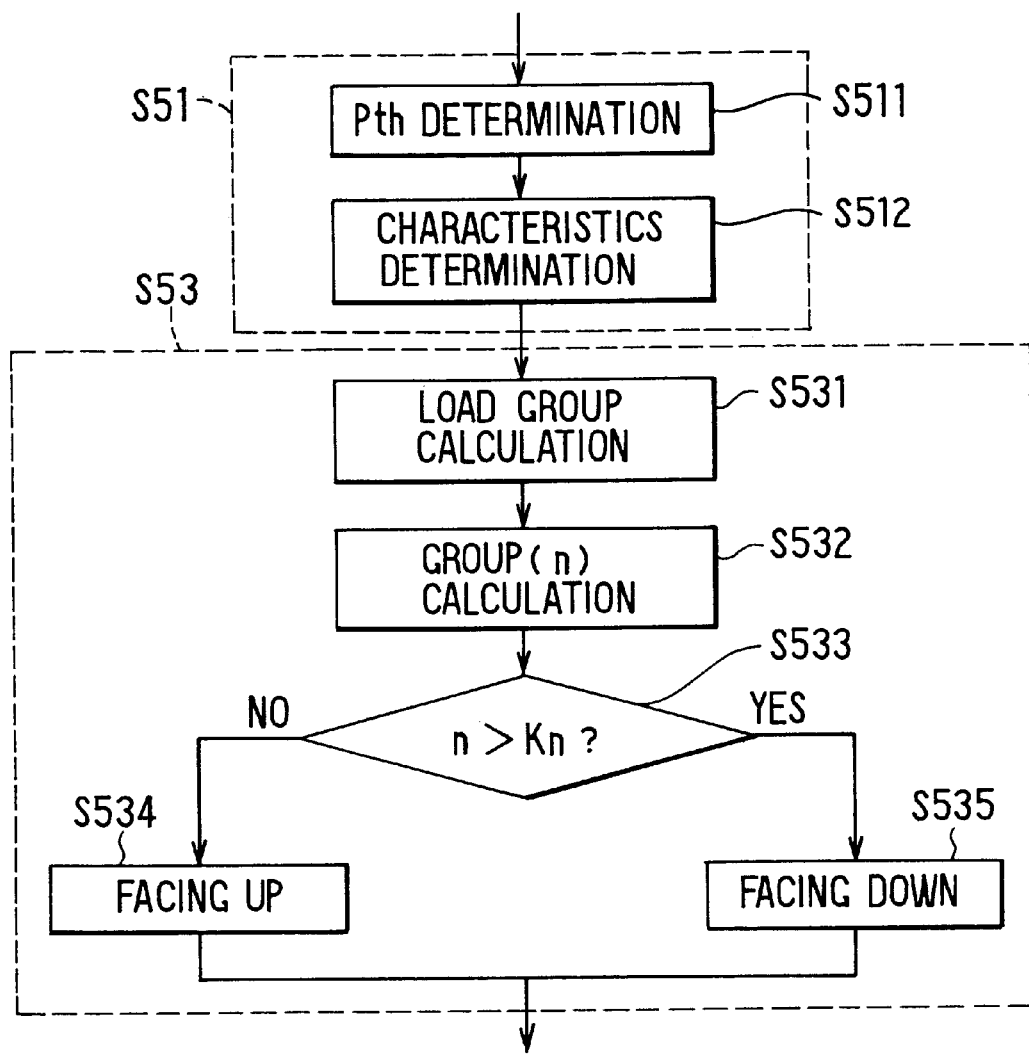
FIG. 10 is a flow diagram showing the determination processing of infant's sleeping posture in the infant condition monitoring system according to the second embodiment.

This embodiment is differentiated from the first embodiment in respect of weight determination step S5 and sleeping posture determination step S5 as shown in FIGS. 8, 9 and 10, so that the infant's weight is calculated when he/she is in less motion, e.g., when he/she is asleep.

Specifically, as shown in FIG. 9 in detail, weight determination step S4 includes steps S401 and S402 in addition to steps S41 and S42 of the first embodiment (FIG. 3). That is, a motion index m is calculated first at step S401. The motion index m is calculated by dividing a pressure change (a sum of absolute values of changes in all the load signals from the pressure sensitive cells 11) per unit time by all the load signal values). This motion index m is compared with a threshold Km at step S402. The threshold Km may be set to 0.05. If YES (m<Km) indicating that the infant is in less motion, the processing proceeds to steps S41 and S42 to determine the infant's weight in the same manner as in the first embodiment. If NO (m>Km) indicating that the infant is in motion, the weight is not calculated because the calculation will result in error.

Further, as shown in FIG. 10 in detail, step S53 is executed in place of step S52 of the first embodiment (FIG. 6). Here, it is to be understood that the characteristics amount is digitized to either "1" or "0" at step S51 (S511 and S512) by using the threshold calculated based on the equation (1). Then, at step S531, a load group or block is calculated at step S531 for each pressure sensitive cell 11 from the digitized results of eight cells surrounding one cell digitized to "1". That is, one load group is defined as a group or block of cells digitized to "1" and surrounded entirely by cells digitized to "0".

Figure 11:
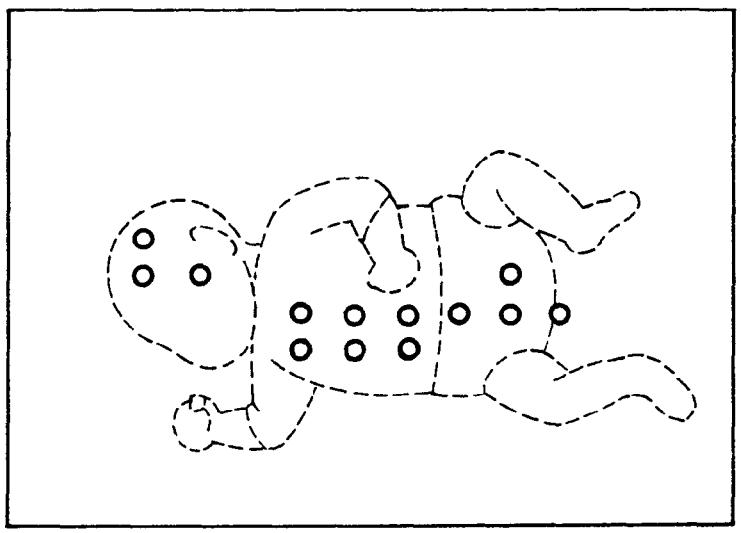
FIG. 11 is a schematic view showing the infant sleeping while lying on his/her back.
Figure 12:
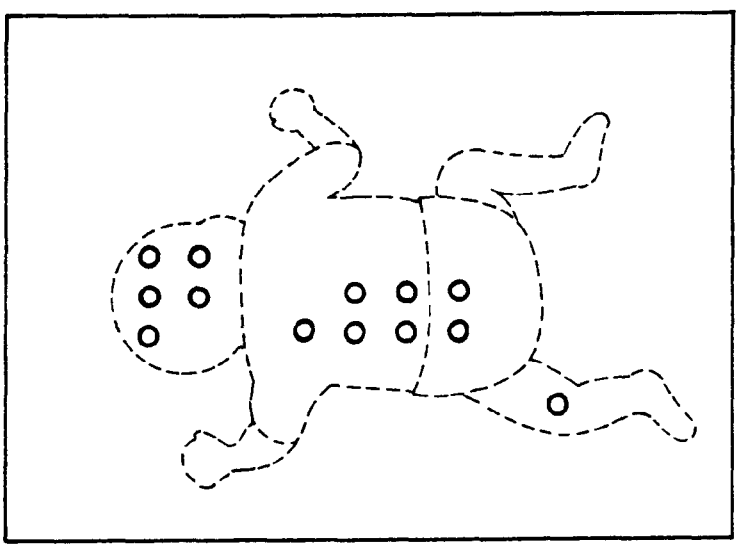
FIG. 12 is a schematic view showing the infant sleeping while lying on his/her stomach.

The number of load groups n is calculated or counted at step S532. This number n is compared with a threshold Kn at step S533. If NO (n<Kn), it is determined at step S534 that the infant is lying on his/her back, that is, facing down, as shown in FIG. 11. If YES (n>Kn), it is determined at step S535 that the infant is lying on his/her stomach, that is, facing down, as shown in FIG. 12.

It is to be noted that the loads indicated by circles in FIG. 10 center at head part and body part as shown in FIG. 11 when the infant is lying on his/her back. In this instance, the number of load groups is two, one at the head part and the other at the body part. On the contrary, the loads decentralize over a wide range as shown in FIG. 12when the infant is lying on his/her stomach, because the loads are also applied at the foot part, knee part, arm part. In this instance, the number of load groups is larger than the case of lying on his/her back.

The above second embodiment provides the following advantage (e) in addition to the above advantages (a) to (d) of the first embodiment.

(e) The infant's weight can be measured accurately, because it is determined when he/she is in less motion. Further, the sleeping posture display in two postures (facing down or not) enables the care provider to recognize it with ease.

The above embodiments may be modified as follows.

The electronic unit 3 and the monitoring unit 4 may be connected through signal wires, and the display may be a television monitor. The breathing condition may be reported by driving a vibrator wound around the care provider's arm, changing the number of lighting of a plurality of light emitting diodes, or displaying a breathing curve on a liquid crystal display device or a CRT. The monitoring unit 4 may be constructed to issue an alarm when the respiration rate deviates from the normal range. The sensor sheet 1 may employ capacitive type cells or strain gage type cells in place of the pressure sensitive cells 11.

The specified frequency range for load signal processing may be varied based on the age of the infant, because the respiration rate varies with age or growth. In this instance, the age of the infant to be monitored may be estimated from the weight of the infant, so that the specified frequency range may be shifted to a lower frequency range as the estimated age increases. For instance, the specified frequency range may be set to 0.37–1.25 Hz (22–75 times of respiration per minute) for infants below one year old, 0.28–0.66 Hz (17–40 times of respiration per minute) for infants between one and two years old, and to lower frequencies as the age increases.

The present invention should not be limited to the above disclosed embodiments and modifications, but may be implemented in other ways without departing from the spirit of the present invention.

What is claimed is:

1. An infant condition monitoring system comprising:

a plurality of load cells, arranged to be contacted by an infant, for producing respectively load signals varying with loads applied from the infant;

breathing signal forming means for selectably receiving a plurality of the load signals and forming a breathing signal;

breathing condition detecting means for detecting a breathing condition of the infant from the breathing signal; and reporting means for reporting the detected breathing condition.

2. The monitoring system as in claim 1, wherein:

the breathing signal forming means is constructed to select from the load cells a reference cell which produces a highest signal intensity in a specified frequency range, and to form the breathing signal from the load signal of the selected reference cell.

3. The monitoring system as in claim 2, wherein:

the breathing signal forming means is constructed to select the load cells which produce the load signals in at least one of same or opposite phase relation with that of the load signal of the selected reference cell, and to form the breathing signal by adding at least one of the load signals of the selected load cells in the same phase relation and inverted signals of the load signals of the selected load cells in the opposite phase relation to the load signal of the selected reference cell.

4. The monitoring system as in claim 2, wherein:

the breathing signal forming means is constructed to frequency-analyze the load signals to select the reference cell as the one which has a largest power spectrum in the specified frequency range.

5. The monitoring system as in claim 1, further comprising:

sleeping posture determining means for determining a sleeping posture characteristics from the load signals of the load cells, and determining a sleeping posture of the infant from the determined sleeping posture characteristics, wherein the reporting means is constructed to report the determined sleeping posture in addition to the breathing condition.

6. The monitoring system as in claim 1, further comprising:

sleeping posture determining means for determining the load cell which senses load in excess of a threshold to determine cell groups each of which is surrounded by the load cells which senses load less than the threshold, and determining a sleeping posture of the infant from the number of the cell groups, wherein the reporting means is constructed to report the determined sleeping posture in addition to the breathing condition.

7. The monitoring system as in claim 1, further comprising:

weight determining means for determining a weight of the infant by integrating the load signals of the load cells, wherein the reporting means is constructed to report the determined weight in addition to the breathing condition.

8. The monitoring system as in claim 1, further comprising:

motion determining means for detecting motion of the infant from changes in the load signals of the load cells and determining a stationary state when the detected motion is less than a threshold; and weight determining means for determining a weight of the infant by integrating the load signals of the load cells when the stationary state is determined, wherein the reporting means is constructed to report the determined weight in addition to the breathing condition.

9. The infant condition monitoring system according to claim 1, wherein the breathing condition detecting means includes means for determining a respiration rate from the breathing signal, and wherein the reporting means is constructed to produce at least one among (A) a display of the determined respiration rate and (B) an output sound varying with a waveform of the breathing signal.

10. The infant condition monitoring system according to claim 1, said system further comprising:

data signal transmitter means connected to the breathing signal forming means for transmitting a data signal including the breathing signal; and data signal receiver means connected to the breathing condition determining means for receiving the data signal wirelessly from the transmitter means.

11. An infant condition monitoring system comprising:

a plurality of load cells, arranged to be contacted by an infant, for producing respectively load signals varying with loads applied from the infant;

breathing signal forming means for forming a breathing signal from the load signals;

breathing condition detecting means for detecting a breathing condition of the infant from the breathing signal; and reporting means for reporting the detected breathing condition, wherein the breathing condition detecting means includes means for determining a respiration rate from the breathing signal; and the reporting means is constructed to produce at least one among (A) a display of the determined respiration rate, and (B) an output sound varying with a waveform pattern of the breathing signal.

12. An infant condition monitoring system comprising:

a plurality of load cells, arranged to be contacted by an infant, for producing respectively load signals varying with loads applied from the infant;

breathing signal forming means for forming a breathing signal from the load signals;

breathing condition detecting means for detecting a breathing condition of the infant from the breathing signal;

reporting means for reporting the detected breathing condition;

data signal transmitter means connected to the breathing signal forming means for transmitting a data signal including the breathing signal; and data signal receiver means connected to the breathing condition determining means for receiving the data signal wirelessly from the transmitter means.

13. A personal condition monitoring method comprising the steps of:

placing a person to be monitored on a sensor sheet having a plurality of load cells arranged at regular intervals over the sensor sheet;

selectably receiving a plurality of load signals from a corresponding plurality of the load cells and forming a breathing signal of the person;

determining a breathing condition of the person from the formed breathing signal; and reporting the determined breathing condition.

14. The monitoring method as in claim 13, wherein:

the breathing signal forming step selects from the load signals one load signal, which varies most responsively to a breathing of the person, and additional load signals, which are in a specified relation with the one load signal, and forms the breathing signal from the selected one and additional load signals.

15. The monitoring method as in claim 13, wherein:

the breathing signal forming step selects some of the load signals which vary in a same phase relation with each other and adds the selected load signals to form the breathing signal.

16. The monitoring method as in claim 13, further comprising the steps of:

determining a sleeping posture of the person from the load signals of the load cells; and displaying the determined sleeping posture on a display.

17. The personal condition monitoring method according to claim 13, wherein:

the breathing condition determining step calculates a respiration rate of the person from the formed breathing signal; and the reporting step comprises at least one among displaying the calculated respiration rate and producing an output signal varying with the formed breathing signal.

18. The personal condition monitoring method according to claim 13, further comprising:

detecting a stationary state of the person from changes in the load signals of the load sensors;

determining a weight of the person from the load signals of the load sensors under the detected stationary state; and displaying the determined weight on a display.

19. A personal condition monitoring method comprising the steps of:

placing a person to be monitored on a sensor sheet having a plurality of load cells arranged at regular intervals over the sensor sheet;

forming a breathing signal of the person from load signals produced by a selected plurality of the load cells;

determining a breathing condition of the person from the formed breathing signal; and reporting the determined breathing condition, wherein:

the breathing condition determining step calculates a respiration rate of the person from the formed breathing signal; and the reporting step comprises at least one among displaying the calculated respiration rate and producing an output signal varying with the formed breathing signal.

20. A personal condition monitoring method comprising the steps of:

placing a person to be monitored on a sensor sheet having a plurality of load cells arranged at regular intervals over the sensor sheet;

forming a breathing signal of the person from load signals produced from the load cells;

determining a breathing condition of the person from the formed breathing signal;

reporting the determined breathing condition;

detecting a stationary state of the person from changes in the load signals of the load sensors;

determining a weight of the person from the load signals of the load sensors under the detected stationary state; and displaying the determined weight on a display.

21. A condition monitoring system for a person comprising:

a sensor sheet including a plurality of load cells each of which is uniformly arranged to produce a load signal varying with a load applied thereto by the person; and an electronic unit connected to the sensor sheet for receiving the load signal of each load cell separately from load signals produced by other load cells of the sensor sheet and for determining a condition of the person from received load signals, the electronic unit including selecting means for selecting the load signals produced by fewer than all of the plurality of load cells for use in determining the condition of the person.

22. The condition monitoring system as in claim 21, wherein the electronic unit includes multiplexing means for selecting the load signals individually and producing the selected load signals serially.

* * * * *